US010857280B2

(12) United States Patent
Wong et al.

(10) Patent No.: US 10,857,280 B2
(45) Date of Patent: Dec. 8, 2020

(54) METHODS OF SYNTHESIZING HYDROUS ZIRCONIUM OXIDE AND OTHER OXIDES

(71) Applicant: Fresenius Medical Care Holdings, Inc., Waltham, WA (US)

(72) Inventors: Raymond J. Wong, Oklahoma City, OK (US); Lucas Fontenelle, Oklahoma City, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1518 days.

(21) Appl. No.: 13/800,317

(22) Filed: Mar. 13, 2013

(65) Prior Publication Data

US 2013/0190168 A1 Jul. 25, 2013

Related U.S. Application Data

(63) Continuation of application No. PCT/US2011/052683, filed on Sep. 22, 2011.

(60) Provisional application No. 61/406,768, filed on Oct. 26, 2010.

(51) Int. Cl.
*B01J 21/06* (2006.01)
*A61M 1/16* (2006.01)
*B01J 20/28* (2006.01)
*B01J 45/00* (2006.01)
*B01J 20/06* (2006.01)

(52) U.S. Cl.
CPC ............ *A61M 1/1654* (2013.01); *B01J 20/06* (2013.01); *B01J 20/28057* (2013.01); *B01J 20/28071* (2013.01); *B01J 20/28083* (2013.01); *B01J 45/00* (2013.01); *A61M 1/1696* (2013.01); *B01J 2220/62* (2013.01)

(58) Field of Classification Search
CPC . B01J 21/00; B01J 21/06; B01J 21/063; B01J 21/066; B01J 31/06; B01J 31/08; B01J 31/65; B01J 31/16; B01J 31/2221; B01J 20/28054; B01J 20/28057; B01J 20/28061; B01J 20/28078; B01J 20/28083; B01J 20/28085; B01J 20/28069; B01J 20/28071; B01J 20/28002; B01J 20/28004; B01J 20/28007; B01J 20/28011; B01J 23/00; A61M 1/654; A61M 1/656; A61M 1/696
See application file for complete search history.

(56) References Cited

U.S. PATENT DOCUMENTS

| | | | |
|---|---|---|---|
| 4,778,671 A | 10/1988 | Wusirika | |
| 6,602,919 B1 | 8/2003 | Collins | |
| 7,252,767 B2 * | 8/2007 | Bortun | B01J 21/06 |
| | | | 210/660 |
| 2002/0112609 A1 * | 8/2002 | Wong | A61M 1/1696 |
| | | | 96/131 |

(Continued)

OTHER PUBLICATIONS

International Search Report and Written Opinion issued in corresponding International Patent Application No. PCT/US2011/052683 dated Apr. 23, 2012 (12 pages).

(Continued)

*Primary Examiner* — Smita S Patel
(74) *Attorney, Agent, or Firm* — Kilyk & Bowersox, PLLC

(57) ABSTRACT

The present invention relates to sol gel hydrous metal oxide particles, such as hydrous zirconium oxide particles, their manufacture, and their use in such applications as sorbent dialysis.

49 Claims, 1 Drawing Sheet

1. Reactor vessel
2. Agitator with speed control
3. Product slurry
4. Mixer of ZOC (or zirconium complex) stream and precipitant stream
5. Zirconium complex solution vessel
6. Precipitant e.g., NaOH vessel
7. Peristaltic pumps with flow control

(56) References Cited

U.S. PATENT DOCUMENTS

| | | | |
|---|---|---|---|
| 2004/0007531 A1 | 1/2004 | Bortun et al. | |
| 2006/0110314 A1* | 5/2006 | Torardi | B82Y 30/00 |
| | | | 423/608 |
| 2006/0135652 A1* | 6/2006 | Kasseh | C08K 3/22 |
| | | | 523/205 |
| 2006/0140840 A1* | 6/2006 | Wong | A61K 33/42 |
| | | | 423/305 |

OTHER PUBLICATIONS

Pan et al., "Preparation of zirconia xerogels and ceramics by sol-gel method and the analysis of their thermal behavior," Thermochimica Acta, vol. 376, 2001, pp. 77-82.

Liang et al., "Polyvinylpyrrolidone/ZrO2-based sol-gel films applied in highly reflective mirrors for inertial confinement fusion," J. Sol-Gel Sci. Technol., vol. 47, 2008, pp. 173-181.

Chatry et al., "The Role of Complexing Ligands in the Formation of Non-Aggregated Nanoparticles of Zirconia," J. Sol-Gel Sci. Technol., vol. 1, 1994, pp. 233-240.

Das et al., "A Novel Chemical Route for the Preparation of Nanocrystalline PZT Powder," Mat. Lett., vol. 45, 2000, pp. 350-355.

* cited by examiner

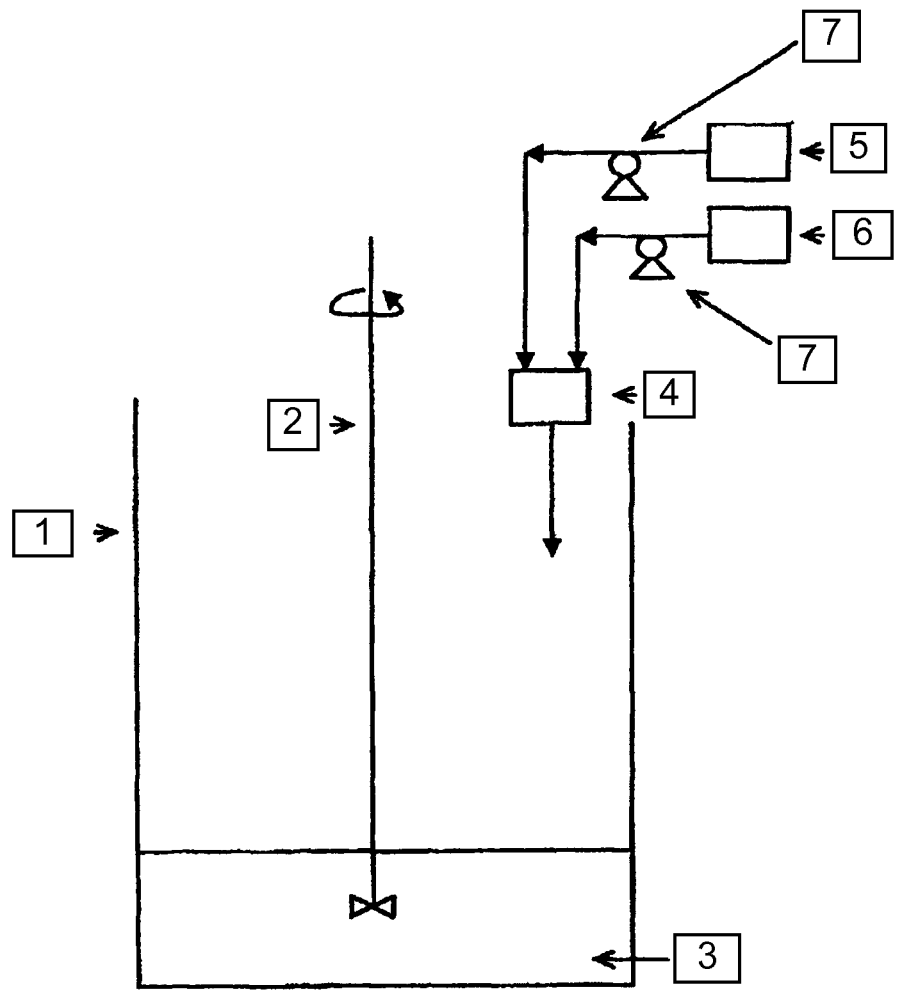
1. Reactor vessel
2. Agitator with speed control
3. Product slurry
4. Mixer of ZOC (or zirconium complex) stream and precipitant stream
5. Zirconium complex solution vessel
6. Precipitant e.g., NaOH vessel
7. Peristaltic pumps with flow control

METHODS OF SYNTHESIZING HYDROUS ZIRCONIUM OXIDE AND OTHER OXIDES

This application is a continuation of International Patent Application No. PCT/US2011/052683, filed on Sep. 22, 2011, which, in turn, claims the benefit under 35 U.S.C. § 119(e) of prior U.S. Provisional Patent Application No. 61/406,768, filed Oct. 26, 2010, which is incorporated in its entirety by reference herein.

BACKGROUND OF THE INVENTION

The present invention relates to hydrous zirconium oxide particles and to methods of making hydrous zirconium oxide particles, such as by sol gel synthesis. The present invention further relates to sol gel hydrous metal oxide particles, such as hydrous zirconium oxide (HZO) particles, their manufacture, and their use in such applications as sorbent dialysis.

Existing hydrous zirconium oxides often are of non-uniform particle size and suffer from low porosity (including mesoporosity) as well as poor BET surface adsorption area and capacity. These defects compromise sorbent dialysis performance and limit the kinds and amounts of toxic ions and organic solutes that can be effectively removed from a bodily fluid. Traditionally, manufacture of hydrous metal oxide particles have been plagued by extensive gelation and agglomeration rendering the oxide less than ideal for dialysis applications. Conventional methods of making HZO by reacting solid zirconium compounds with alkali or by conversion of basic zirconium carbonate by heat, yield HZO with low BET surface area that cannot bind anions that well, such as sulfate and nitrate, and cannot bind that well to toxic compounds originating from a waste compound of the body's metabolism. Conventional methods of sol gel synthesis using zirconium alkoxide or other zirconium compounds with precipitants make it difficult, if not impossible, to obtain a homogenous product with respect to both particle size and adsorption quality.

Accordingly, there is a need for an improved method of synthesizing hydrous zirconium oxide particles that can be carried out on a manufacturing scale.

There is a further need for an improved method of synthesizing hydrous zirconium oxide particles that overcomes one or more of the above-mentioned disadvantages.

There is also a need for better performing and more uniform hydrous metal oxide particles with improved mesoporosity as well as methods for making the same that decrease or eliminate gelation and agglomeration.

SUMMARY OF THE PRESENT INVENTION

A feature of the present invention is to provide a method of synthesizing hydrous zirconium oxide particles and other metal oxides by a sol gel technique that avoids the above-mentioned disadvantages.

Another feature of the present invention is to provide a method of synthesizing hydrous zirconium oxide particles and other metal oxides by a sol gel technique that avoids the creation of soft gel particles and that avoids agglomeration of the particles.

Another feature of the present invention is to provide a method of synthesizing hydrous zirconium oxide particles and other metal oxides by a sol gel technique that provides particles having a desirable hardness, particle size, particle size range, shape, porosity, BET surface area for adsorption, and/or adsorption capacity.

Additional advantages of the present invention will be set forth in part in the description that follows, and in part will be apparent from the description, or may be learned by practice of the present invention. The goals and advantages of the present invention will be realized and attained by means of the elements particularly pointed out in the appended claims.

To achieve the above noted goals and in accordance with the purposes of the present invention, as embodied and broadly described herein, the present invention provides a method for synthesizing hydrous zirconium oxide particles by providing a solution of zirconium oxychloride preferably in an aqueous solvent, adding at least one oxygen-containing additive to the solution, wherein the oxygen-containing additive can form a soluble zirconium complex in the solution of zirconium oxychloride and thereby reduce hydration of the zirconium ions, and then combining the solution with at least one precipitant base to obtain zirconium hydroxide particles by sol gel precipitation.

The present invention further provides a method of synthesizing hydrous zirconium oxide particles having a controlled particle size or particle size distribution. The method includes reacting zirconium oxychloride with at least one precipitant base to obtain hydrous zirconium oxide particles by sol gel precipitation. For instance, the method can include providing a reaction vessel having an agitator and adding a solution of zirconium oxychloride and a solution of base simultaneously to the reaction vessel so that zirconium ions react with the base to obtain hydrous zirconium oxide particles by sol gel precipitation. The particle size and/or particle size distribution of the hydrous zirconium oxide particles obtained are controlled by controlling at least one of the following parameters: the method of mixing the base and zirconium oxychloride together, the amount of dispersant used as an additive, the rate at which the solution of zirconium oxychloride is added to the reaction vessel, the rate at which the solution of base is added to the reaction vessel, the pH of the solution of base, the concentration of zirconium oxychloride and base in the reaction vessel, and the speed of the agitator.

The present invention also provides a method of making hydrous metal oxide particles. In accordance with this method, at least one oxygen-containing additive is combined with at least one water soluble metal salt in an aqueous solvent to form a first solution wherein the oxygen-containing additive forms a complex with metal ions in the first solution. The first solution is combined with a precipitant base to obtain hydrous metal oxide particles by sol gel precipitation.

The present invention further relates to hydrous metal oxide particles, such as hydrous zirconium oxide particles, made by the processes of the present invention and/or having improved adsorption capacity, improved BET surface area, improved mesoporosity, improved particle size, and/or other characteristics not achieved previously.

It is to be understood that both the foregoing general description and the following detailed description are exemplary only and are not restrictive of the present invention, as claimed.

The accompanying drawing, which is incorporated in and constitute a part of this application, illustrate some of the features of the present invention and together with the description, serve to explain the principles of the present invention.

BRIEF DESCRIPTION OF DRAWING

FIG. 1 is a flow chart/schematic showing an example of one set up that can be used in a process of the present invention.

DETAILED DESCRIPTION OF THE PRESENT INVENTION

The present invention relates to hydrous metal oxides, such as hydrous zirconium oxide, and to methods of making the hydrous metal oxides. In a particularly useful example, the hydrous metal oxide is a hydrous zirconium oxide, which is a desirable component used in fluid purifications, such as in dialysis applications. The hydrous zirconium oxide is a useful component, especially for sorbent cartridges in dialysis. In the present invention, the hydrous metal oxide, and more specifically the hydrous zirconium oxide, is a sol gel hydrous metal oxide particle. The hydrous metal oxide particle, such as the hydrous zirconium oxide, can be in the form of hydrous metal oxide particles and/or the hydrous metal oxide can be in the form of a polymeric network. Furthermore, as a temporary intermediate product or as an end product, the hydrous metal oxide particles, such as hydrous zirconium oxide particles, can include at least one oxygen-containing additive that forms a soluble metal complex (e.g., zirconium complex) with the metal ion(s) of the hydrous metal oxide. This can be a complex in a metal ion solution, such as a zirconium oxychloride solution, with reduced coordinated water molecules. The hydrous metal oxide, in a sol gel form, for instance, can have attached at least one polar functional group.

The hydrous metal oxide, such as the hydrous zirconium oxide, can be a homogenous product that has one or more desirable properties, such as improved porosity, improved BET surface area, improved adsorption capacity, improved selectivity, and the like. The hydrous metal oxide, such as the hydrous zirconium oxide particles, can have a uniform particle size range, for instance, from about 40 microns to about 90 microns, such as from 45 microns to 90 microns, 50 microns to 85 microns, 55 microns to 85 microns, and the like. This uniform particle size range can be an average particle size range and/or can be a distribution of the particle size.

The present invention relates in part to a method of synthesizing hydrous zirconium oxide particles by a sol gel technique (and referring to zirconium as an example), using a solution of zirconium oxychloride in which the hydration of zirconium ions in the solution has been reduced. This can be accomplished, for example, by the use of at least one additive in the zirconium oxychloride solution to change the zirconium ions in the solution from a highly hydrated monomeric form to a soluble polymeric zirconium complex with a high number of polymer units and a reduced water of hydration.

To explain how an additive can affect the characteristics of hydrous zirconium oxide formed in a sol gel process, it helps to understand the nature of the zirconium ions in a zirconium oxychloride solution in the absence of an additive. Zirconium ions in a zirconium oxychloride solution by itself are highly hydrated zirconium species with 4-8 molecules of $H_2O$ coordinated with each Zr atom. The hydrated ions may form polymeric units ranging from a monomer, $ZrOOH^+$, to a tetramer, $Zr_4(OH)_8^{+8}$, depending on the concentration of the solution. As a precipitant base is mixed with a zirconium oxychloride solution at room temperature, a sol gel hydrous zirconium oxide precipitate is formed at a very rapid rate, trapping a large number of coordinated water molecules (or hydronium ions since the lattice $H^+$ can combine with $H_2O$ molecules to form $H_3O^+$) within the gel particle to form a soft gel. As discussed above, these soft gel particles have a tendency to agglomerate as the slurry gets denser and when the material is packed on a filter during filtration or on trays during drying.

Using at least one additive preferably forms new zirconium polymeric species in solution having a reduced number of coordinated water molecules and a high polymer unit so that when these Zr polymeric species react with a precipitant base, the problems described above that arise from excessive hydration do not occur. In particular, the reaction of zirconium ions with a precipitant base is slowed, which allows for the concentration of reactants to be more easily controlled, thereby allowing for the particle size and/or particle size distribution of the particles formed by precipitation to be controlled. Because of the reduced water content, the particles formed by precipitation are harder and less prone to agglomeration and have a more refined molecular structure. If the additive that is used also has properties of an emulsifying agent, it is possible to improve the shape of the particles formed by precipitation from irregular to roughly spherical. Doing so may reduce the agglomeration problem during drying, allowing for the formation of a free-flowing powder. Even if the particle size is kept small, the flow performance for column application can be improved.

Except as otherwise provided herein, the synthesis of hydrous zirconium oxide particles by the sol-gel process may be carried out according to known sol-gel techniques. For example, the aqueous solution used to initially dissolve the zirconium oxychloride can be water purified to remove ionic impurities such as trace metals by reverse osmosis (RO water) or by any other method that provides a low enough level of contaminants to be acceptable for the intended end use of the hydrous zirconium oxide particle or may be deionized water.

The additive used in the present invention is capable of displacing water molecules that are coordinated to zirconium ions in an aqueous solution of zirconium oxychloride and that can preferably bridge zirconium ions to form a water soluble polymer species.

In the present invention, the hydrous metal oxide, such as the hydrous zirconium oxide, can be present as hydrous metal oxide particles, such as hydrous zirconium oxide particles, having one or more of the characteristics and/or properties and/or features described herein. The hydrous metal oxide, such as the hydrous zirconium oxide, can be a complex, wherein at least one oxygen-containing additive, as described herein, which can include at least one polar group and/or a charge group is present as a soluble ligand that forms a complex with the metal ion of the hydrous metal oxide. Either form of the hydrous metal oxide, namely having the oxygen-containing additive present or not, can further be modified to include at least one functional group, such as at least one polar functional group. The functional group can be attached to the hydrous metal oxide, such as by being entrapped, absorbed, adsorbed, ionic bonded, and/or hydrogen bonded, and the like. Typically, no covalent bonding occurs with regard to the functional group and its attachment to the hydrous metal oxide. More than one type of functional group can be attached in this manner. The functional group can be or serve as a chelating agent or as a complexing agent or as a cationic exchange group or as an anionic exchange group or as a surfactant, or any combination of these properties. Examples of the functional groups include, but are not limited to, acids, amines, sulfates, sulfonic acids, and/or surfactants, and the like. More specific examples include, but are not limited to, EDTA, sulfonic acid, hydroxylamine, lauryl sulfate, and/or hydroxybenzene sulfonic acid, and the like. More details are provided below. The attachment of a functional group, such as a polar functional group, can enhance various properties, such as sulfate adsorption capacity and/or other properties desirable in the purification of fluids.

In more detail, the present invention in part relates to hydrous metal oxide particles that contain at least one hydrous metal oxide, and at least one oxygen-containing additive; wherein the oxygen-containing additive includes a polar group and/or a charged group; and wherein the oxygen-containing additive forms a soluble complex with the metal ion of the hydrous metal oxide. The metal ion of the hydrous metal oxide ion can be any suitable metal ion able to complex with an oxygen-containing additive. The metal ion can be a zirconium ion, a hafnium ion, a titanium ion, a tin ion, or a lead ion, or any combination thereof. When the metal ion is a zirconium ion, the resulting hydrous metal oxide (HMO) is a hydrous zirconium oxide (HZO).

Any appropriate oxygen-containing additive or combination of additives can be used, which can complex with the metal ion of the hydrous metal oxide. The additive(s) used in the present invention is generally capable of displacing water molecules that are coordinated to zirconium ions or other metal ions in an aqueous solution of a soluble metal salt, such as zirconium oxychloride and that can, as an option, bridge zirconium ions or other metal ions to form a water soluble polymer species. The additive can be a solid, liquid, and/or gas. The additive can be a compound, mixture, polymer, and the like. Additives that can be used in the present invention include inorganic and organic compounds that contain oxygen atoms that are positioned in the compound so that they are available to displace coordinated water molecules and so that zirconium atoms or other metal atoms can be bridged to form polymeric species. The additive can also lead to the formation of polymer species that are water soluble. More than one additive can be used, e.g., mixtures. The oxygen-containing additive can form a temporary or permanent complex with the metal ion of the hydrous metal oxide. The oxygen-containing additive can have an average molecular weight of from about 10 Da to about 100,000 Da or more, or from about 25 Da to about 50,000 Da, from about 35 Da to about 35,000 Da, from about 40 Da to about 4000 Da, from about 50 Da to about 500 Da, from about 75 Da to about 350 Da, or from about 100 Da to about 200 Da. Organic and/or inorganic additives can be used as additives. The additive can be or include a polyol and an ester. The oxygen-containing additive can be or include acetic acid, soda ash, polyvinyl alcohol, tartaric acid, EDTA, glycerol, and/or sodium dodecyl sulfate, or any combination thereof. Other examples of oxygen-containing additives include those with bulky groups, an overall large size, long chains, or any combination thereof. The oxygen-containing additive can contain at least one surfactant. Dodecyl sulfate is an example of one suitable surfactant. The oxygen-containing additive can contain at least one dispersant. One example of a suitable dispersant is tartaric acid. The oxygen-containing additive can be selected so as to also function as the dispersant, as in the case of tartaric acid or similar acids.

Examples of inorganic additives include, for example, sulfates such as sodium sulfate or sulfuric acid, soda ash, and/or carbonates. Examples of organic additives include, for example, compounds, such as alcohols (e.g., butanol), polyalcohols or polyols (such as glycerol, ethylene glycol, sorbitol or mannitol), cellulose (e.g., ethyl cellulose), carboxylates, carboxylic acids (such as acetic acid or hexanoic acid or tartaric acid or polycarboxylic acids), esters (e.g., isopropyl butyrate), ketones, aldehydes, hydroxylamine (e.g., long chain hydroxylamine), organic sulfates, such as dodecyl sulfate, and/or peroxides, such as hydrogen peroxide. Specific, non-limiting examples of additives that can be used are sodium sulfate, glycerol, isopropanol, sodium carbonate and mixtures of any of these. The additive can be or include at least one large molecular weight polymer, surfactant, chelating agent, complexing agent, and/or silane coupling agent that can have an attached functional group, such as an alkyl group, and the like. Examples include, but are not limited to, EDTA (Mwt. 292.24), lauryl sulfate (Mwt. 288.38), polyvinyl alcohol (PVA) (Mwt. 124,000-186,000), sulfonic acid (Mwt.>>200), or an alkoxy silane, such as an ethoxy silane.

Examples of low molecular weight, oxygen containing, monofunctional, organic additives that can be used in the present invention include alcohols having the following formula: R—OH, wherein R is a $C_{1-6}$ alkyl group, such as a $C_{1-3}$ alkyl group, and carboxylic acids having the following formula: R—COOH, wherein R is a $C_{1-6}$ alkyl group, such as a $C_{1-3}$ alkyl group. The alcohol and carboxylic acids can be non-branched or branched isomers. Specific, non-limiting examples of additives that can be used are methanol, ethanol, propanol, isopropanol, acetic acid, propionic acid, or combinations thereof. Examples of low molecular weight include, but are not limited to, a molecular weight of from about 1 to about 10, of from about 10 to about 100, from about 20 to about 80, or from about 30 to about 60 Daltons.

Typical examples of additives and the zirconium polymer species formed in a zirconium oxychloride solution are as follows:

TABLE 1

Additives

TYPICAL ZR POLYMERIC SPECIES IN SOLUTION

INORGANIC ADDITIVES

1. Sulfates (sulfuric acid, sodium sulfate, etc.)

$$HO-Zr(H_2O)(H_2O)(H_2O)-O-S(=O)(=O)-O-Zr(H_2O)(H_2O)(H_2O)-O-S(=O)(=O)-O-Zr$$

2. Carbonate $(Zr_2O_3^{2+})$ complex

ORGANIC ADDITIVES

1. Alcohol ROH

TABLE 1-continued

Additives

TYPICAL ZR POLYMERIC SPECIES IN SOLUTION

2. Glycerol

3. Carboxylate or carboxylic acid

4. Ketones; aldehydes

5. Organic sulfates (dodecyl sulfate)

M wt. 288.38

The at least one oxygen-containing additive can be present in an amount of from about 0.1 wt % to about 10 wt % or more, such as from about 1 wt % to about 10 wt % by weight of the zirconium oxychloride or other soluble metal salt (e.g, Group IV B metal salt) (e.g., 1 wt % to 8 wt %, or 2 wt % to 7 wt %, or 3 wt % to 5 wt % additive). Other amounts and molar ratios below and above these ranges can be used. The oxygen-containing additive can form a soluble polymer complex with zirconium ions. The additive can be of low molecular weight. The additive can be monofunctional.

Set forth below are examples of various complexes that can be formed:

1. Zirconium Complex with Lauryl Sulfate

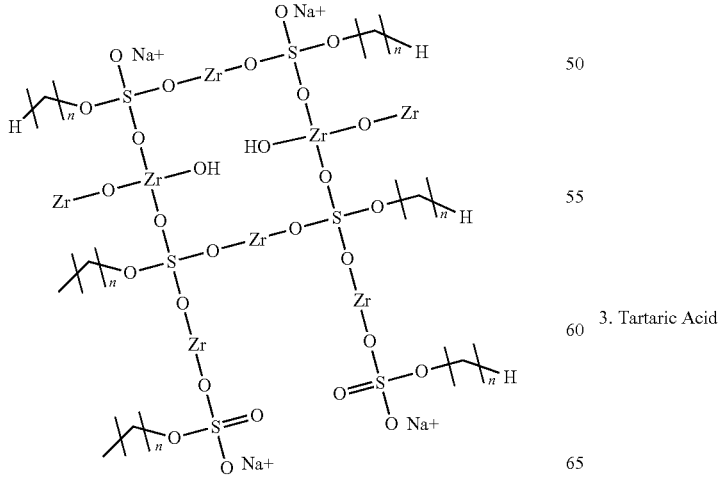

2. Ethylene Diamine Tetracetic Acid or EDTA

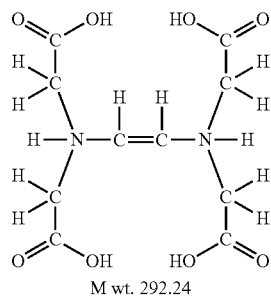

M wt. 292.24

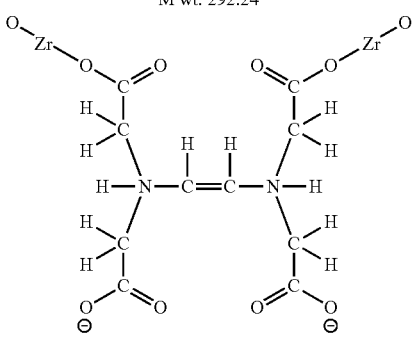

Zirconium Complex with EDTA

3. Tartaric Acid

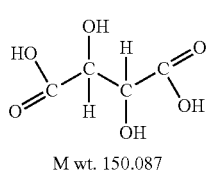

M wt. 150.087

-continued

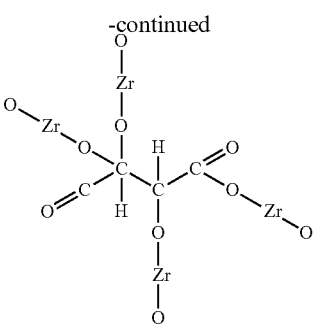

Zirconium Complex with Tartaric Acid

4. Polyvinyl Alcohol or PVA (87-89% hydrolyzed)
↓
M wt. 124,000-186,000

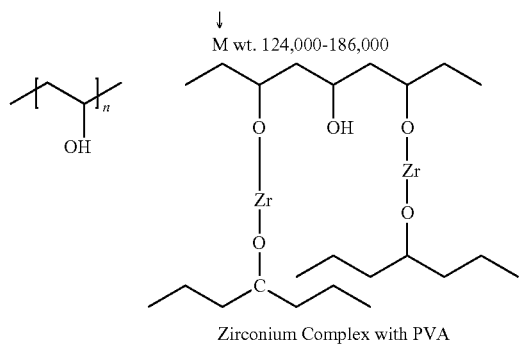

Zirconium Complex with PVA

5. Glycerol

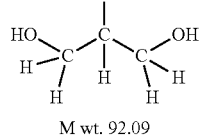

M wt. 92.09

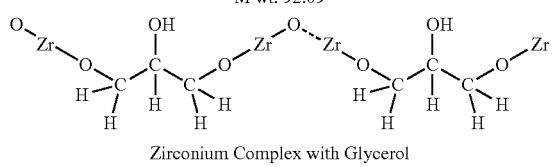

Zirconium Complex with Glycerol

Hydrous Zirconium Oxide (HZO) Bonded with EDTA for Chelation with Cations

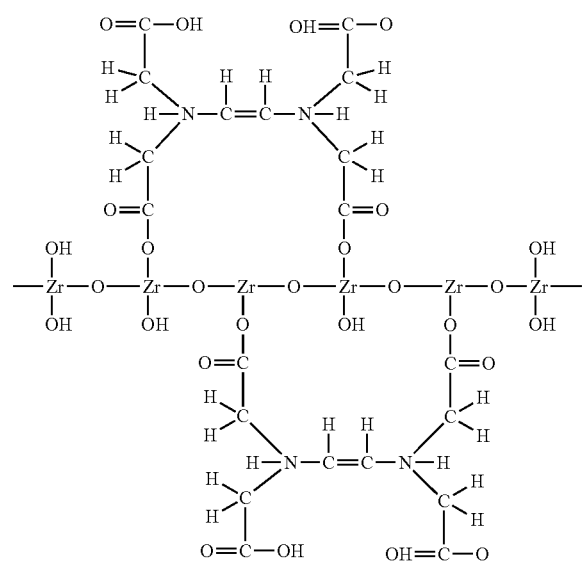

Hydrous Zirconium Oxide (HZO) Bonded with Hydroxyamine for Chelation with Anions

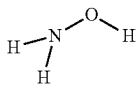

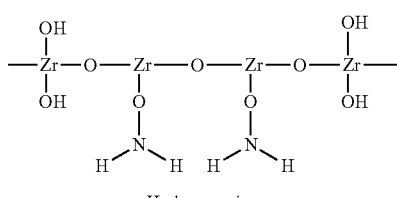

Hydroxyamine

The hydrous metal oxide particles can have a particle size range of from about 0.5 to about 500 microns or more, of from about 1 to about 100 microns, of from about 1.5 to about 50 microns, or of from about 2 to about 25 microns. The hydrous metal oxide particles can have an average particle size range of from about 30 microns to about 90 microns, such as from 30 microns to 80 microns, from 31 microns to 70 microns, from 32 microns to 60 microns, from 33 microns to 50 microns, from 30 microns to 40 microns, and the like. The hydrous metal oxides of the present invention can have a maximum particle size of over 100 microns, such as over 140 microns, or over 150 microns, or over 160 microns, or over 170 microns, or over 180 microns, such as from 140 to 200 microns. In the present application, all particle size distributions are set forth as a % as determined or as based on the number of particles having that size for the total number of particle counted. The hydrous metal oxide particles can have a particle size distribution in % (by count or by number or by amount) of:

a) a size of less than 25 microns (e.g., less than 10 microns or less than 5 microns)—less than 10% (e.g., less than 5% or less than 1%);

b) a size of 5 microns or more (e.g., more than 10 microns, more than 25 microns, more than 30 microns, more than 50 microns)—90% or more, 92% or more, 95% or more, 97% or more; and/or c) a size of 0.5 micron to about 500 microns (e.g., about 1 micron to about 100 microns, about 10 microns to about 500 microns, about 15 microns to about 250 microns, about 25 microns to about 100 microns, about 35 microns to about 100 microns)—90% or more, 93% or more, 95% or more, 97% or more, 99% or more.

As a further example, the hydrous metal oxide particles can have a particle size distribution as follows:

a) a size of less than 35 microns: 10% or less, 5% or less, 4% or less, 3% or less, 2% or less, 0.5% to 4%;

b) a size of from 35 microns to 100 microns: 80% or more, 85% or more, 90% or more, 92% or more, 95% or more, 97% or more, 95% to 99%;

c) a size of over 100 microns: 10% or less, 5% or less, 4% or less, 3% or less, 2% or less, 0.5% to 4%.

The HZO can have a particle size distribution of less than 25% in the range of less than about 25 microns, less than 5% in the range of more than about 100 microns, and more than 70% in the range of from about 25 microns to about 100 microns.

The HZO particle distribution can be less than 14% in the range of less than 16 microns, less than 8% in the range of about 158 microns, and more than 76% in the range of about 30 microns, for example, 28 microns to 32 microns.

The hydrous metal oxide particles can have a pore volume of at least 0.09 mL/g, and/or a monolayer volume of at least 37 mL/g (STP), and/or a range of from about 20 to about 80 nm pore size content of at least 10%. The hydrous metal oxide particles can have an average BET surface area of at least about 100 m$^2$/g, such as from about 100 m$^2$/g to about 300 m$^2$/g, 120 m$^2$/g to about 300 m$^2$/g, 150 m$^2$/g to 275 m$^2$/g, 200 m$^2$/g to 350 m$^2$/g.

The hydrous metal oxide is capable of binding at least one ion that is a phosphate, a sulfate, a nitrate, or any combination thereof. The hydrous metal oxide is capable of binding one or more waste products comprising creatinine, uric acid, ammonium ($NH_4^+$), beta-2 micro-globulin, bilirubin, citrate, phenol, methanol, or any combination thereof. The hydrous metal oxide can have a phosphate binding capacity of from about 0.1 mg/g HMO to about 100 mg/g HMO, from about 1 mg/g HMO to about 100 mg/g HMO, from about 5 mg/g HMO to about 80 mg/g HMO, from about 10 mg/g HMO to about 50 mg/g HMO, or from about 15 mg/g HMO to about 25 mg/g HMO, when exposed to 100 mg/dL of phosphate. The hydrous metal oxide can have a sulfate binding capacity of from about 0.1 mg/g HMO to about 100 mg/g HMO, from about 1 mg/g HMO to about 100 mg/g HMO, from about 5 mg/g HMO to about 80 mg/g HMO, from about 10 mg/g HMO to about 50 mg/g HMO, or from about 15 mg/g HMO to about 25 mg/g HMO, when exposed to 100 mg/dL of sulfate. The hydrous metal oxide can have a nitrate binding capacity of from about 0.1 mg/g HMO to about 100 mg/g HMO, from about 1 mg/g HMO to about 100 mg/g HMO, from about 5 mg/g HMO to about 80 mg/g HMO, from about 10 mg/g HMO to about 50 mg/g HMO, or from about 15 mg/g HMO to about 25 mg/g HMO, when exposed to 100 mg/dL of nitrate. The hydrous metal oxide can have an ammonium ion binding capacity of from about 0.1 mg/g HMO to about 100 mg/g HMO, from about 1 mg/g HMO to about 100 mg/g HMO, from about 5 mg/g HMO to about 80 mg/g HMO, from about 10 mg/g HMO to about 50 mg/g HMO, or from about 15 mg/g HMO to about 25 mg/g HMO, when exposed to 100 mg/dL of ammonium ion.

As a feature of the present invention, a hydrous zirconium oxide composition is provided that contains a water-soluble hydrous zirconium oxide polymer in an aqueous solution, wherein the polymer is formed by combining, in an aqueous solvent, zirconium oxychloride with at least one oxygen-containing additive that is capable of forming a complex with zirconium ions, wherein the hydrous zirconium oxide composition, when dried, has a particle size distribution of less than 25% in the range of less than about 25 microns, less than 5% in the range of more than about 100 microns, and more than 70% in the range of from about 25 microns to about 100 microns.

The hydrous metal oxide particles of the present invention can be optionally loaded with an ion (anion or cation), such as one of lesser or least affinity. The ion employed can be a chloride ion or an acetate ion (e.g., HZO—Cl or HZO-Acetate). A dialysis cartridge housing hydrous metal oxide particles as a component can be made, such as a portable dialysis system having a container that contains the hydrous metal oxide particles.

The HMO, and particularly the HZO of the present invention can be used in any application where HZO is used and can be used as the HZO layer or as an additional HZO layer in sorbent cartridges, such as the ones described in U.S. Published Patent Application No. 2002-0112609 and U.S. Pat. No. 6,878,283 B2, and in Sorb's REDY cartridge (e.g., see "Sorbent Dialysis Primer," COBE Renal Care, Inc. Sep. 4, 1993 edition, and "Rx Guide to Custom Dialysis," COBE Renal Care, Inc. Revision E, September, 1993), all incorporated in their entirety by reference herein. All embodiments using HZO in these published applications are embodiments of the present application wherein the HZO of the present invention is used. For example purposes only, various filter media sections within a tubular housing or cartridge can be used with the HZO particles of the present invention. The housing or cartridge can include a granular activated carbon section, an immobilized enzyme section, a powdered alumina ($Al_2O_3$) section, a zirconium phosphate, and/or a section that includes a mixture of hydrous zirconium oxide of the acetate form and sodium zirconium carbonate, or sodium zirconium carbonate alone. For hemodialysis, a filter medium adapted to remove chlorine from tap water is preferred unless highly purified water is used as a base for the dialysate. The medium can be activated carbon. Activated carbon can be used as a filter medium to bind heavy metals, oxidants, and chloramines. An immobilized enzyme such as urease can be used in a filter medium to convert urea to ammonium carbonate by enzymatic conversion. Urease can be immobilized by adsorption, covalent bonding, intermolecular cross-linking, entrapment within cross-linked polymers, microencapsulation, and containment within a semipermeable membrane device. Alumina ($Al_2O_3$), activated carbon, anion exchange resins, and diatomaceous earth can be used as adsorbents. Urease can be used to covalently bond water-insoluble polymers to form enzyme-polymer conjugates via activation procedures or reactive polymers. Multifunctional reagents, for example, glutaraldehyde and hexamethylene diamine can be used to affect intermolecular cross-linking of urease. Urease can be entrapped within a cross-linked polymer, such as, for example, polyacrylamide gel. Urease can be microencapsulated using, for example, nylon, cellulose nitrate, ethyl cellulose, or polyamide. Urease can be contained within some permeable membrane device, such as, for example, AMICOM ultra-filtration cells, available from Fisher Scientific, Pittsburgh, Pa., or DOW hollow fiber beaker device, from The Dow Chemical Co., Midland, Mich. The use of activated carbon to remove chlorine, if used, should precede the immobilized enzyme medium because chlorine can deactivate the enzyme. Cation exchange materials can be used to bind ammonium, calcium, magnesium, potassium, and other cations as well as toxic trace metals in tap water. Another function of these filter media can be to convert carbonate from urea hydrolysis to bicarbonate. Such cation exchange materials can include zirconium phosphate, titanium phosphate, or zeolite. Anion exchange filter media bind phosphate, fluoride, and other heavy metals. Bi-products of the anion exchange filter media can include acetate and bicarbonate, which also corrects for metabolic acidosis of a patient's blood. Such filter media can include hydrous zirconium oxide of the acetate form, hydrous silica, stannic oxide, titanium oxide, antimonic acid, hydrous tungsten oxide, or sodium zirconium carbonate.

The present invention further relates to methods of making hydrous metal oxides particles, such as the particles described above and elsewhere herein. The method can include the steps of combining at least one oxygen-containing additive with at least one water soluble metal salt in an aqueous solvent to form a first solution wherein the oxygen-containing additive forms a complex with metal ions in the first solution; and combining the first solution with at least one precipitant to obtain hydrous metal oxide particles by sol gel precipitation. The metal ion of the metal oxide can include a zirconium ion, a hafnium ion, a titanium ion, a tin ion, or a lead ion, or any combinations thereof. The metal ion can be a zirconium ion and the soluble metal salt (e.g., Group IV B metal salt) can be a zirconium salt, such as zirconium oxychloride. Any appropriate salt can be used that yields water soluble metal cations. Examples include oxychlorides, acetates, and/or nitrates.

The precipitant can have a molarity of from about 0.1 moles/L or less to about 20 moles/L or more, from about 0.5 moles/L to about 20 moles/L, from about 2.5 moles/L to about 10 moles/L, from about 5 moles/L to about 20 moles/L, or from about 9.5 moles/L to about 19 moles/L. The precipitant can include an alkaline solution. The alkaline solution included can be a hydroxide. The alkaline solution can be or include sodium hydroxide. The precipitant can be from about 5% to about 50% by weight, or from about 25% to about 50% by weight sodium hydroxide. The soluble metal salt can be zirconium oxychloride. The soluble metal salt and precipitant can be introduced at a molar ratio of soluble metal salt to precipitant of from about 0.1:1 or less to about 0.5:1 or more. The precipitant and zirconium oxychloride can be introduced at a molar ratio of about 3.9:1 to about 8.0:1. The soluble metal salt can be present in the aqueous solvent at a concentration of from about 0.1 g/ml or less to about 2.5 g/ml or more, from about 0.5 g/ml to about 2 g/ml, from about 0.1 g/ml to about 0.5 g/ml, or from about 0.25 g/ml to about 2.0 g/ml. Examples of aqueous solvents include deionized water and reverse osmosis water. The zirconium oxychloride can be present in the aqueous solvent at a concentration of from about 1 g/ml to about 1.67 g/ml.

The soluble metal salt can be dissolved in the aqueous solvent and the oxygen-containing additive can be added to form the first solution. The soluble metal salt can be present in the aqueous solvent at a saturation concentration. The oxygen-containing additive can be dissolved in the aqueous solvent and then the soluble metal salt can be added to form the first solution. The oxygen-containing additive can be present in the first solution in a molar amount sufficient so that substantially all of the metal ions in the solution are converted to a complex. The oxygen-containing additive can be present in a molar amount sufficient to avoid or at least minimize gelation and/or agglomerization. The oxygen-containing additive can form a soluble complex with the metal ion of the hydrous metal oxide. The oxygen-containing additive, as an option, forms a temporary complex with the metal ion of the hydrous metal oxide in the solution such that the additive is removable with a washing step from the product after precipitation. The oxygen-containing additive can form a permanent complex with the metal ion of the hydrous metal oxide. An aqueous solvent, such as water, can be added to the zirconium oxychloride and/or other soluble metal salt, and then the oxygen-containing additive and solvent can be added to the resulting zirconium oxychloride and/or other soluble metal salt solution.

The method of the present invention can utilize a technique of mixing the streams of the zirconium (or other metal) complex solution from zirconium oxychloride (ZOC) (or other soluble metal salt) and the precipitant, e.g., sodium hydroxide, simultaneously before immediate delivery of the product slurry mixed stream into the reactor containing initially a small amount of precipitant. The product slurry in the reactor is then continuously agitated at a slow rate designed to control particle size of the product. The mixing of ZOC solution and precipitant streams should be based on the proper design of the following parameters to achieve desirable product composition including particle size and adsorption quality: (i) Proper concentration of ZOC and precipitant, e.g., NaOH; (ii) Proper ratio of amount of ZOC to amount of precipitant, e.g., NaOH; proper flow rate of ZOC stream and precipitant stream to be mixed; and amount of additive or dispersant used in ZOC solution.

The first solution and the precipitant can be combined by providing the precipitant in an aqueous solution and adding at least part of the first and at least part of the precipitant solution simultaneously to a reaction vessel so that the concentration of precipitant is kept constant in the reaction vessel during a period of time that the precipitant is added to the reaction vessel. The first solution can be combined with the precipitant by providing a reaction vessel and simultaneously adding the first solution and a diluted solution of precipitant to the reaction vessel. The properties of hydrous metal oxide particles obtained by sol gel precipitation can optionally be altered by adjusting the pH of the precipitant solution used. In addition to the simultaneous addition of the soluble metal salt and precipitant solutions, other parameters, including the manner of addition of the soluble metal salt solution and the manner of mixing of the reactants, can be controlled to provide a more efficient reaction and to control the particle size range. A spray head can be used as the inlet for the additive-containing solution of soluble metal salt so that the solution can be added to the reaction vessel in the form of droplets, thereby providing a more efficient reaction. The soluble metal salt solution and the precipitant solution can be mixed at least partially in air before entering a reaction vessel.

The solution of soluble metal salt can be in the form of droplets before it is combined with precipitant. The first solution can be obtained and the precipitant solution can be combined so that metal ions and precipitant are present in a molar ratio of from about 0.1 or less to about 10 or more of metal to precipitant, such as from about 0.5 to about 10 metal to precipitant, from about 1 to about 5 of metal to precipitant, or from about 5 to about 25 of metal to precipitant.

The reaction vessel can include an agitator. The reaction vessel can be equipped to agitate the reactants as they are added to the reaction vessel and as the reaction proceeds, thereby providing for more efficient mixing and avoiding differences in particle sizes caused by differing concentrations of reactants in different sections of the reaction vessel. The reaction vessel can include an agitator, such as, for example, an agitator having more than one set of blades attached to a shaft at different levels, so that the reactants in the reaction vessel are thoroughly mixed at all levels. A multi-impeller agitator can be used, such as an agitator that has three sets of blades, each set attached to a shaft at a different level. The use of an agitator to control or reduce agglomeration is optional. If an agitator is used, commercial agitators, including multi-impeller agitators, can be used. An agitation rate of from about 5 rpm or less to about 80 rpm or less, or from about 10 rpm to about 80 rpm, or about 20 rpm to about 80 rpm, or about 30 rpm to about 40 rpm, or about 50 rpm to about 70 rpm can be used. A low agitation speed, such as from about 20 rpm to about 40 rpm, can be used, which can assist in avoiding agglomeration without causing a break-up of gel particles. With a single-impeller agitator, a speed of about 60 to about 70 rpm, for example, can be employed. For any given agitator, the optimum speed is dependent on variables such as the tank size, shape, baffles, impeller size, and the like. Other methods of agitation or mixing can be used. Agitation is ideally performed at a slow continuous rate designed to control particle size of the product.

A slurry containing at least a hydrous metal oxide gel precipitate can be formed in accordance with the methods of the present invention. The slurry can be agitated. The product slurry can be filtered, such as after mixing is completed. The product can be washed with water such as reverse osmosis or deionized water (alkaline wash). A filter cake can be formed. The filter cake can be transferred back to deionized water to form a second slurry. The second slurry can be titrated to a lower pH value, such as in a range of from about pH 0.5 or less to about pH 12 or more, from about pH 1 to about pH 10, from about pH 2 to about pH 8, or from about pH 4 to about pH 6, by addition of acid to remove precipitant cations (acid wash). The titrated or acid-washed slurry can be filtered. The resulting hydrous metal oxide particles can be isolated and dried to obtain a free flowing powder. The drying can be performed at any suitable temperature. For example, drying can be performed at about 40° F. or less to about 140° F. or more, from about 50° F. to about 100° F., from about 65° F. to about 90° F., or at about 80° F. The product can be dried until the moisture of the product is from about 1% or less to about 40% or more, from about 5% to about 40%, from about 10% to about 30%, and from about 18% to about 22% (based on wt %) Loss on Drying by moisture balance (LOD) in the form of free-flowing powder.

The steps of the methods of the present invention can be carried out at any suitable temperature or temperatures. One or more steps can be carried out at ambient or room temperature (20° C. to 40° C.), and/or at lower or higher temperatures. Mild heating can be employed to avoid formation of zirconia. Heat treatment can also be helpful to achieve superior crystallinity and/or purity. The product can be boiled at about 100° C. for about an hour or two. A slurry can be agitated during heat (hydrothermal) treatment.

A method of making hydrous metal oxide particles having a controlled particle size is provided that involves forming hydrous metal oxide particles by sol gel precipitation by any method of the present invention, and controlling at least one of the following parameters to affect particle size or particle size distribution of the hydrous metal oxide particles: rate at which the solution of soluble metal salt is added to the reaction vessel (e.g., in the range of from about 10 ml/min to about 100 ml/min), rate at which the precipitant solution is added to the reaction vessel (e.g., in the range of from about 15 ml/min to about 150 ml/min), pH of the precipitant solution (e.g., greater than 10), concentration of soluble metal salt (e.g., from about 1 g/ml to about 2 g/ml) and precipitant in the reaction vessel (e.g., from about 10 mol/l to about 20 mol/l), or speed of the agitator (e.g., from about 5 rpm to about 80 rpm) or any combinations thereof.

A method of making hydrous zirconium oxide particles is provided that can include the steps of combining at least one oxygen-containing additive with zirconium oxychloride in an aqueous solvent to form a first solution wherein the oxygen-containing additive forms a complex with zirconium ions in the solution; and combining the first solution with precipitant to obtain hydrous zirconium oxide particles by sol gel precipitation, wherein the oxygen-containing additive is described earlier, or can be a surfactant, acetic acid, soda ash, polyvinyl alcohol, tartaric acid, EDTA, glycerol, sodium dodecyl sulfate, or any combination thereof.

A method of making hydrous zirconium oxide particles is provided that includes adding a solution of zirconium oxychloride and a precipitant solution simultaneously to a reaction vessel to obtain hydrous zirconium oxide particles by sol gel precipitation. The present invention further includes a composition containing hydrous metal oxide particles, wherein the particles are formed by any method of the present invention.

FIG. 1 provides an example of a flow chart/schematic of a process set-up for making HZO particles or other hydrous metal oxide particles, where reactor vessel 1 receives the reactants, an agitator with optional speed control 2 can be used, the product slurry 3 is in the reactor vessel 1, a vessel 5 containing the zirconium complex solution (or other metal complex solution), a vessel 6 containing the precipitant (e.g., NaOH), a mixer 4 can be used to mix the materials from vessels 5 and 6, and the materials from vessels 5 and 6 can be pump via pumps 7 for each respective vessels 5 and 6.

As a further example, when HZO is formed, the structure of the sol gel (in its numerous stages) can be or include:

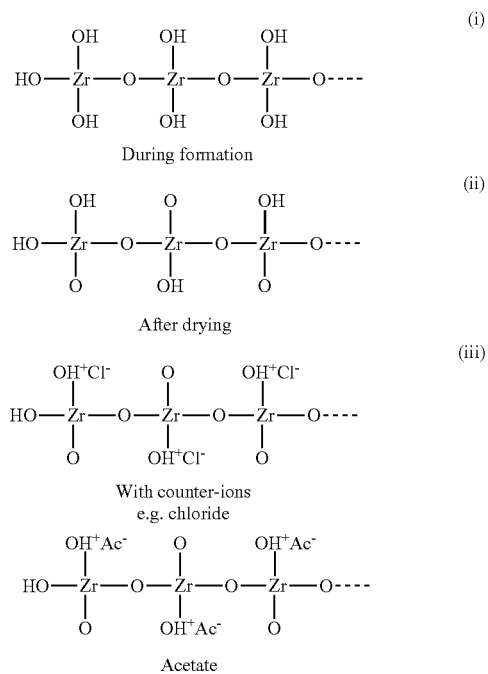

The HZO can be in a salt form, such as HZO-acetate or HZO-chloride, or other counterions.

The present invention includes the following aspects/embodiments/features in any order and/or in any combination:

1. The present invention relates to a hydrous metal oxide particles comprising:
   at least one hydrous metal oxide; and
   at least one oxygen-containing additive;
   wherein the oxygen-containing additive comprises at least one polar group or a charged group or both; and
   wherein the oxygen-containing additive is present as a soluble ligand that forms a complex with the metal ion of the hydrous metal oxide.
2. The hydrous metal oxide particles of the preceding or following embodiment/feature/aspect, wherein a metal ion of the hydrous metal oxide comprises a zirconium ion, a hafnium ion, a titanium ion, a tin ion, or a lead ion.
3. The hydrous metal oxide particles of the preceding or following embodiment/feature/aspect, wherein the metal ion is a zirconium ion.
4. The hydrous metal oxide particles of the preceding or following embodiment/feature/aspect, wherein the oxygen-containing additive comprises a molecular weight from about 50 to about 500 Da.

5. The hydrous metal oxide particles of the preceding or following embodiment/feature/aspect, wherein the oxygen-containing additive comprises a surfactant.

6. The hydrous metal oxide particles of the preceding or following embodiment/feature/aspect, wherein the oxygen-containing additive comprises a dispersant.

7. The hydrous metal oxide particles of the preceding or following embodiment/feature/aspect, wherein the dispersant is tartaric acid.

8. The hydrous metal oxide particles of the preceding or following embodiment/feature/aspect, wherein the oxygen-containing additive comprises acetic acid, soda ash, polyvinyl alcohol, tartaric acid, EDTA, glycerol, sodium dodecyl sulfate, or any combination thereof.

9. The hydrous metal oxide particles of the preceding or following embodiment/feature/aspect, wherein the hydrous metal oxide particles have a particle size range of from about 2 to about 200 microns.

10. The hydrous metal oxide particles of the preceding or following embodiment/feature/aspect, wherein the hydrous metal oxide particles have a particle size distribution of less than 25% in the range of less than about 25 microns, less than 5% in the range of more than about 100 microns, and more than 70% in the range of from about 25 microns to about 100 microns.

11. The hydrous metal oxide particles of the preceding or following embodiment/feature/aspect, having a pore volume of at least 0.09 mL/g, or a monolayer volume of at least 37 mL/g (STP), or a 20-80 nm pore size content of at least 10%.

12. The hydrous metal oxide particles of the preceding or following embodiment/feature/aspect, wherein the hydrous metal oxide particles have an average BET surface area of at least 100 m$^2$/g.

13. The hydrous metal oxide particles of the preceding or following embodiment/feature/aspect, wherein the hydrous metal oxide is capable of binding at least one anion that is phosphate, sulfate, nitrate or any combination thereof.

14. The hydrous metal oxide particles of the preceding or following embodiment/feature/aspect, wherein the hydrous metal oxide is capable of binding one or more waste product comprising creatinine, uric acid, NH4+, beta-2 micro-globulin, bilirubin, citrate, phenol, methanol, or any combination thereof.

15. The hydrous metal oxide particles of the preceding or following embodiment/feature/aspect, wherein the oxygen-containing additive forms a temporary complex with the metal ion of the hydrous metal oxide.

16. The hydrous metal oxide particles of the preceding or following embodiment/feature/aspect, wherein the oxygen-containing additive forms a permanent complex with the metal oxide of the hydrous metal oxide.

17. A dialysis system comprising a cartridge that contains the hydrous metal oxide particles of any one of the preceding claims.

18. A portable dialysis system comprising a container that contains the hydrous metal oxide particles of any one of the preceding claims.

19. A hydrous zirconium oxide composition comprising a water-soluble hydrous zirconium oxide polymer in an aqueous solution, wherein the polymer is formed by combining, in an aqueous solvent, zirconium oxychloride with at least one oxygen-containing additive that is capable of forming a complex with zirconium ions, wherein the hydrous zirconium oxide composition, when dried, has a particle size distribution of less than 25% in the range of less than about 25 microns, less than 5% in the range of more than about 100 microns, and more than 70% in the range of from about 25 microns to about 100 microns.

20. The present invention relates to a method of making hydrous metal oxide particles according to any preceding or following embodiment/feature/aspect comprising:

combining at least one oxygen-containing additive with at least one water soluble metal salt in an aqueous solvent to form a first solution wherein the oxygen-containing additive forms a complex with metal ions in the first solution; and combining the first solution with at least one precipitant to obtain hydrous metal oxide particles by sol gel precipitation.

21. The method according to any preceding or following embodiment/feature/aspect, wherein a metal ion of the metal oxide comprises a zirconium ion, a hafnium ion, a titanium ion, a tin ion, or a lead ion.

22. The method according to any preceding or following embodiment/feature/aspect, wherein the metal ion is a zirconium ion and the soluble metal salt is a zirconium salt.

23. The method according to any preceding or following embodiment/feature/aspect, wherein the soluble metal salt is zirconium oxychloride.

24. The method according to any preceding or following embodiment/feature/aspect, wherein the precipitant has a molarity of from about 5 moles/L to about 25 moles/L.

25. The method according to any preceding or following embodiment/feature/aspect, wherein the precipitant is an alkali solution.

26. The method according to any preceding or following embodiment/feature/aspect, wherein the alkali solution is sodium hydroxide.

27. The method according to any preceding or following embodiment/feature/aspect, wherein the soluble metal salt is zirconium oxychloride and the zirconium oxychloride and precipitant are introduced at a molar ratio of metal salt to precipitant of from about 0.1:1 to about 0.5:1.

28. The method according to any preceding or following embodiment/feature/aspect, wherein the soluble metal salt is zirconium oxychloride and the zirconium oxychloride is present in the aqueous solvent at a concentration of from about 0.5 to about 2.0 g/ml.

29. The method according to any preceding or following embodiment/feature/aspect, wherein the aqueous solvent is deionized water or reverse osmosis water.

30. The method according to any preceding or following embodiment/feature/aspect, wherein the soluble metal salt is dissolved in the aqueous solvent and then the oxygen-containing additive is added to form the first solution.

31. The method according to any preceding or following embodiment/feature/aspect, wherein the soluble metal salt is present in the aqueous solvent at a saturation concentration.

32. The method according to any preceding or following embodiment/feature/aspect, wherein the oxygen-containing additive is dissolved in the aqueous solvent and then the soluble metal salt is added to form the first solution.

33. The method according to any preceding or following embodiment/feature/aspect, wherein the oxygen-containing additive is present in the first solution in a molar amount sufficient to prevent gelation of the particles.

34. The method according to any preceding or following embodiment/feature/aspect, wherein the oxygen-containing additive forms a soluble complex with the metal ion of the hydrous metal oxide.

35. The method according to any preceding or following embodiment/feature/aspect, wherein the oxygen-containing additive forms a temporary complex with the metal ion of the hydrous metal oxide in the solution such that the additive is removable from the particles with a washing step after precipitation.

36. The method according to any preceding or following embodiment/feature/aspect, wherein the oxygen-containing additive forms a permanent complex with the metal ion of the hydrous metal oxide.

37. The method according to any preceding or following embodiment/feature/aspect, wherein the first solution and the precipitant are combined by providing the precipitant in an aqueous solution and adding at least part of the first and at least part of the precipitant solution simultaneously to a reaction vessel so that the concentration of precipitant is kept constant in the reaction vessel during a period of time that the precipitant is added to the reaction vessel.

38. The method according to any preceding or following embodiment/feature/aspect, wherein said first solution is simultaneously added with a diluted solution of precipitant to the reaction vessel.

39. The method according to any preceding or following embodiment/feature/aspect, wherein the reaction vessel includes an agitator.

40. The method according to any preceding or following embodiment/feature/aspect, wherein a slurry containing at least a hydrous metal oxide gel precipitate is formed, and wherein the slurry is agitated.

41. The method according to any preceding or following embodiment/feature/aspect, further comprising filtering the product slurry after mixing.

42. The method according to any preceding or following embodiment/feature/aspect, further comprising washing the product with deionized water (alkaline wash).

43. The method according to any preceding or following embodiment/feature/aspect, further comprising forming a filter cake.

44. The method according to any preceding or following embodiment/feature/aspect, further comprising transferring the filter cake back to deionized water to form a second slurry.

45. The method according to any preceding or following embodiment/feature/aspect, further comprising titrating the second slurry to lower pH to a value in a range of from about pH 2 to about pH 8 by addition of acid to remove precipitant cations (acid wash).

46. The method according to any preceding or following embodiment/feature/aspect, further comprising filtering the titrated or acid-washed slurry and drying the product until the moisture of the product is from about 10% to about 40% LOD in the form of free-flowing powder.

47. The method according to any preceding or following embodiment/feature/aspect, further comprising isolating and drying the resulting hydrous metal oxide particles to obtain a free flowing powder.

48. The method according to any preceding or following embodiment/feature/aspect, wherein the solution of soluble metal salt is in the form of droplets before it is combined with precipitant.

49. The method according to any preceding or following embodiment/feature/aspect, wherein the first solution obtained and the precipitant solution are combined so that metal ions and precipitant are present in a molar ratio of from about 0.1 to about 1 of metal to precipitant.

50. The present invention relates to a method of making hydrous metal oxide particles having a controlled particle size comprising:
    forming hydrous metal oxide particles by sol gel precipitation by the method of any one of the preceding claims, and controlling at least one of the following parameters to affect particle size or particle size distribution of the hydrous metal oxide particles: rate at which the solution of soluble metal salt is added to the reaction vessel, rate at which the precipitant solution is added to the reaction vessel, pH of the precipitant solution, concentration of soluble metal salt and precipitant in the reaction vessel, or speed of the agitator, or any combination thereof.

51. The present invention relates to a method of making hydrous zirconium oxide particles comprising:
    combining at least one oxygen-containing additive with zirconium oxychloride in an aqueous solvent to form a first solution wherein the oxygen-containing additive forms a complex with zirconium ions in the solution; and
    combining the first solution with precipitant to obtain hydrous zirconium oxide particles by sol gel precipitation, wherein the oxygen-containing additive is a surfactant, acetic acid, soda ash, polyvinyl alcohol, tartaric acid, EDTA, glycerol, sodium dodecyl sulfate, or any combination thereof.

52. The present invention relates to a method of making hydrous zirconium oxide particles comprising: adding a solution of zirconium oxychloride and a precipitant solution simultaneously to a reaction vessel to obtain hydrous zirconium oxide particles by sol gel precipitation.

53. The present invention relates to a composition comprising hydrous metal oxide particles, wherein the particles are formed by the method of any one of the preceding claims.

54. The hydrous metal oxide particles according to any preceding or following embodiment/feature/aspect, further comprising at least one functional group attached to said hydrous metal oxide particles.

55. The hydrous metal oxide particles according to any preceding or following embodiment/feature/aspect, wherein said at least one functional group comprises at least one polar functional group.

56. The hydrous metal oxide particles according to any preceding or following embodiment/feature/aspect, wherein said functional group comprises a surfactant, an acid, an amine, a sulfate, or any combination thereof.

57. The hydrous metal oxide particles according to any preceding or following embodiment/feature/aspect, wherein said functional group is EDTA, sulfonic acid, hydroxy amine, lauryl sulfate, hydroxyl benzene sulfonic acid, or any combination thereof.

58. The present invention relates to a hydrous metal oxide particle, wherein said hydrous metal oxide particle has at least one of the following characteristics:
    a) a sulfate adsorption capacity of 5 mg/g;
    b) a BET surface area of at least 100 $m^2/g$;
    c) a total pore volume of at least 0.09 mL/g;
    d) a pore size of at least 6 nm;
    or any combination thereof.

59. The hydrous metal oxide particles according to any preceding or following embodiment/feature/aspect, wherein said hydrous metal oxide particles have at least one functional group attached thereto.

60. The hydrous metal oxide particles according to any preceding or following embodiment/feature/aspect, wherein the hydrous metal oxide particles have a particle size range of from about 2 to about 200 microns.

61. The hydrous metal oxide particles according to any preceding or following embodiment/feature/aspect, wherein the hydrous metal oxide particles have a particle size distribution of less than 25% in the range of less than about 25 microns, less than 5% in the range of more than about 100 microns, and more than 70% in the range of from about 25 microns to about 100 microns.

62. The hydrous metal oxide particles according to any preceding or following embodiment/feature/aspect, having a pore volume of at least 0.09 mL/g, or a monolayer volume of at least 37 mL/g (STP), or a 20 to 80 nm pore size content of at least 10%.

63. The hydrous metal oxide particles according to any preceding or following embodiment/feature/aspect, wherein said at least one functional group comprises at least one polar functional group.

64. The hydrous metal oxide particles according to any preceding or following embodiment/feature/aspect, wherein said functional group comprises a surfactant, an acid, an amine, a sulfate, or any combination thereof.

65. The hydrous metal oxide particles according to any preceding or following embodiment/feature/aspect, wherein said functional group is EDTA, sulfonic acid, hydroxy amine, lauryl sulfate, hydroxyl benzene sulfonic acid, or any combination thereof.

66. The hydrous metal oxide particle according to any preceding or following embodiment/feature/aspect, wherein said hydrous metal oxide particle has at least one of the following characteristics:
   a) a sulfate adsorption capacity of 5 mg/g;
   b) a BET surface area of at least 100 m$^2$/g;
   c) a total pore volume of at least 0.09 mL/g;
   d) a pore size of at least 6 nm; or any combination thereof.

67. The hydrous metal oxide particles according to any preceding or following embodiment/feature/aspect, wherein said hydrous metal oxide particles have at least one functional group attached thereto.

The present invention can include any combination of these various features or embodiments above and/or below as set forth in sentences and/or paragraphs. Any combination of disclosed features herein is considered part of the present invention and no limitation is intended with respect to combinable features.

The following examples are given to illustrate the nature of the invention. It should be understood, however, that the present invention is not to be limited to the specific conditions or details set forth in these examples.

EXAMPLES

Example 1

Preparation of Sol Gel HZO by Using 1% Tartaric Acid as Additive to ZOC

The synthesis consisted of the following steps:

Step 1—500 g zirconium oxychloride octahydrate (ZOC) was dissolved in 300 ml DI or RO water by magnetic stirring in a 1 L reservoir (A) until the solution was clear;

Step 2—5 g tartaric acid (1 wt % of ZOC amount) was then dissolved in 100 ml DI or RO water in a small beaker to obtain a clear solution and afterwards added to the ZOC solution prepared in Step 1 slowly with magnetic stirring until the precipitate formed as re-dissolved completely to form a clear solution of partial zirconium tartarate complex.

Step 3—800 ml 50% NaOH (Technical Grade) solution was introduced in a 2 L reservoir (B) and another 200 ml 50% NaOH in a 3 L reactor vessel equipped with a motor/stainless steel agitator setup.

Step 4—With the agitator of the reactor on at slow speed (~40 RPM), the zirconium tartarate complex solution from reservoir (A) and the NaOH solution from reservoir (B) were simultaneously pumped at room temperature by roller pumps to a junction where the two streams mixed in air before the mixed stream of produced viscous gel was discharged into the reactor. The flow rate of the zirconium solution was about 10 ml/min and the flow rate of NaOH was such that the mixing of the two solutions in the reservoirs was completed simultaneously at the end. Upon slow agitation, the mixed stream of produced viscous gel first formed a precipitated pulp of soft gel, which then immediately broke up and dispersed to form hardened gel particles with particle size dependent on the concentrations of NaOH, ZOC and agitation speed.

Step 5—Agitation of the slurry was continued slowly for 15 minutes to allow the gel particles to harden. Then vacuum filtration was followed to recover the product. The product was then rinsed in the filter with 1 L DI or RO water to remove the excess Na$^+$, Cl$^-$, OH$^-$, and released tartarate from the complex. The concentrate NaOH should have extracted the tartarate out completely during the alkaline wash.

Step 6—The filter cake after rinsing was discharged to 500 ml DI or RO water in a vessel to form a slurry by slow agitation at <40 RPM. The pH of the slurry was monitored, which was then titrated with glacial acetic acid until the pH was 6.0.

Step 7—The titrated product was then vacuum filtered and the filter cake was rinsed with 1 L DI or RO water to remove the excess Na$^+$ The rinsed filter cake was transferred to a tray dryer and the material was dried to 18-22% LOD at mild temperature. The dried product was in the form of free-flowing powder with average particle size of about 33 microns and 14% less than 16 microns and 17% larger than 174 microns. The particle size can be improved further to be more uniform in the range of 35-45 microns by adjusting the concentrations of NaOH, ZOC, amount of tartaric acid as additive to ZOC, and agitation speed. The product also had a moisture level of 18% LOD; BET surface area 160 m$^2$/g; pore size/pore volume of 6 nm/0.0913 cc/g and sulfate adsorption capacity of 16 mg SO$_4^{2-}$/g HZO.

Thus by simultaneous direct mixing of the NaOH and ZOC streams before discharge into the reactor, and with tartaric acid as the additive to ZOC, uniform particle size sol gel HZO was obtained that was free from agglomeration and gelation, and with high BET surface area, porosity and subsequently enhanced sulfate adsorption capacity, not being affected by decreasing concentration of ZOC for the one-sided addition reaction (i.e. when NaOH is added to ZOC bath) causing non-uniform particle size and quality.

Example 2

Example 1 was repeated by using (i) acetic acid in the amount about 1 wt % of ZOC; (ii) soda ash in the amount about 1 wt % of ZOC; and (iii) sodium sulfate in the amount about 1 wt % of ZOC as additives to ZOC and the sulfate adsorption capacity of each product was compared to that using tartaric acid as the additive in Example 1. It was found that additives with lower molecular weight than tartaric acid also had a smaller sulfate adsorption capacity due to the smaller BET surface area and pore size/pore volume as shown below:

| Additives | M wt | Sulfate Adsorption Capacity |
|---|---|---|
| Acetic acid | 60 | 11.04 mg/g HZO |
| Soda ash | ~106 | 7.57 mg/g HZO |

-continued

| Additives | M wt | Sulfate Adsorption Capacity |
|---|---|---|
| Sodium sulfate | 142 | 14.89 mg/g HZO |
| Tartaric acid | 150.087 | 15.96 mg/g HZO |

Example 3

Example 1 was repeated by using (i) EDTA in the amount about 1 wt % of ZOC; (ii) PVA in the amount about 0.5 wt % ZOC and (iii) sulfonic acid in the amount about 0.5 wt % ZOC and lauryl sulfate (sodium dodecyl sulfate) in the amount about 1 wt % of ZOC as additives to ZOC and the sulfate adsorption capacity of each was compared to that using tartaric acid as the additive in Example 1. It was found that additives with higher molecular wt. than tartaric acid also had higher sulfate adsorption capacity due to the larger BET surface area and pore size/pore volume as shown below:

| Additives | M wt | Sulfate Adsorption Capacity |
|---|---|---|
| EDTA | 292.24 | 19.83 mg/g HZO |
| PVA | 124,000-186,000 | 22.04 mg/g HZO |
| Sulfonic acid | 152 | 17.71 mg/g HZO |
| Lauryl sulfate | 288.38 | 20.8 mg/g HZO |
| Tartaric acid | 150.087 | 15.96 mg/g HZO |

Example 4

Example 3 was repeated and the finished dried products were soaked in the following solutions containing reagents with polar functional groups for 30 minutes.
 (i) 1000 ml EDTA solution in DI or RO water at a concentration of 2.5 g EDTA/100 ml (complexing agent);
 (ii) 1000 ml sulfonic acid solution in DI or RO water at a concentration of 5 g sulfonic acid/100 ml (cation exchange functional group);
 (iii) 1000 ml hydroxyamine in DI or RO water at a concentration of 52 g hydroxyamine/200 ml (anion exchange functional group);
 (iv) 1000 ml lauryl sulfate (sodium dodecyl sulfate) in DI or RO water at a concentration 1 g SDS/100 ml (surfactant)
 (v) 1000 ml hydroxylbenzene sulfonic acid solution in DI or RO water at a concentration 5 g hydroxylbenzene sulfonic acid/100 ml (cation exchange functional group).

The treated products were then vacuum filtered, briefly rinsed and dried at mild temperature to free-flowing powder at LOD 18-22%. It was found that sol gel HZO with polar functional groups introduced for attachment tended to increase the binding sites and hence the sulfate adsorption as compared to Example 3 as shown below:

| HZO with Attachment of Polar Functional Group | Properties | Sulfate Adsorption Capacity |
|---|---|---|
| EDTA | chelating or complexing agent | 21.4 mg/g HZO |
| Sulfonic acid | cationic exchange group | 19.19 mg/g HZO |
| Hydroxyamine | anionic exchange group | 22.8 mg/g HZO |
| Lauryl Sulfate | surfactant | 20.52 mg/g HZO |
| Hydroxylbenzene sulfonic acid | cationic exchange group | 18.07 mg/g HZO |

General Comparison of Adsorption Quality for Sulfate

| | |
|---|---|
| HZO Comparative product — HZO.Ac sulfate adsorption capacity | 4 mg/g HZO |
| Sol gel HZO of present invention vs. comparative | (10-22) mg/g HZO vs. 4 mg/g HZO |
| Inventive large mol wt additive vs. inventive low mol wt additive | 22 mg/g HZO vs. 10 mg/g HZO |
| with attachment of polar groups or complexing ions | >20 mg/g HZO |

BET Surface Area, Pore Size/Pore Volume Data of Sol Gel HZO
BET surface area of sol gel HZO using 1 wt % tartaric acid as additive to ZOC: 160 m$^2$/g HZO
BET surface area of comparative HZO.Ac: ~10 m$^2$/g HZO
Total pore volume of sol gel HZO using 1% tartaric acid as additive to ZOC: 0.0913 ml/g
Pore size: ~6 nm.
As shown in the above data, the sol gel HZO of the present invention is superior to a comparative HZO without an oxygen-containing additive.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:
1. Hydrous metal oxide particles comprising:
 at least one hydrous metal oxide; and
 at least one oxygen-containing additive;
 wherein the oxygen-containing additive comprises at least one polar group or a charged group or both; and
 wherein the oxygen-containing additive is present as a soluble ligand that forms a complex with a metal ion of the hydrous metal oxide, wherein the metal ion of the hydrous metal oxide is a zirconium ion, the hydrous metal oxide particles have a sulfate adsorption capacity of 10 mg/g to 50 mg/g and a phosphate binding capacity of from 0.1 mg/g to 100 mg/g, the hydrous metal oxide particles have an average BET surface area of at least 100 m$^2$/g, and the hydrous metal oxide particles have a particle size distribution of less than 25% in the range of less than about 25 microns, less than 5% in the range of more than about 100 microns, and more than 70% in the range of from about 25 microns to about 100 microns.

2. The hydrous metal oxide particles of claim 1, wherein the oxygen-containing additive comprises a molecular weight from about 50 to about 500 Da.

3. The hydrous metal oxide particles of claim 1, wherein the oxygen-containing additive comprises a surfactant.

4. The hydrous metal oxide particles of claim 1, wherein the oxygen-containing additive comprises a dispersant.

5. The hydrous metal oxide particles of claim 4, wherein the dispersant is tartaric acid.

6. The hydrous metal oxide particles of claim 1, wherein the oxygen-containing additive comprises acetic acid, soda ash, polyvinyl alcohol, tartaric acid, EDTA, glycerol, sodium dodecyl sulfate, or any combination thereof.

7. The hydrous metal oxide particles of claim 1, wherein the hydrous metal oxide particles have a particle size range of from about 2 to about 200 microns.

8. The hydrous metal oxide particles of claim 1 having a pore volume of at least 0.09 mL/g, or a monolayer volume of at least 37 mL/g (STP), or a 20-80 nm pore size content of at least 10%.

9. The hydrous metal oxide particles of claim 1, wherein the hydrous metal oxide particles have a nitrate binding capacity of from 0.1 mg/g to 100 mg/g.

10. The hydrous metal oxide particles of claim 1, wherein the hydrous metal oxide is capable of binding one or more waste product comprising creatinine, uric acid, NH4+, beta-2 micro-globulin, bilirubin, citrate, phenol, methanol, or any combination thereof.

11. The hydrous metal oxide particles of claim 1, wherein the oxygen-containing additive forms a temporary complex with the metal ion of the hydrous metal oxide.

12. The hydrous metal oxide particles of claim 1, wherein the oxygen-containing additive forms a permanent complex with the metal oxide of the hydrous metal oxide.

13. A dialysis system comprising a cartridge that contains the hydrous metal oxide particles of claim 1.

14. A portable dialysis system comprising a container that contains the hydrous metal oxide particles of claim 1.

15. The hydrous metal oxide particles of claim 1, further comprising at least one functional group attached to said hydrous metal oxide particles.

16. The hydrous metal oxide particles of claim 15, wherein said at least one functional group comprises at least one polar functional group.

17. The hydrous metal oxide particles of claim 15, wherein said functional group comprises a surfactant, an acid, an amine, a sulfate, or any combination thereof.

18. The hydrous metal oxide particles of claim 15, wherein said functional group is EDTA, sulfonic acid, hydroxy amine, lauryl sulfate, hydroxyl benzene sulfonic acid, or any combination thereof.

19. The hydrous metal oxide particles of claim 1, wherein the hydrous metal oxide particles have a sulfate adsorption capacity of 10 mg/g to 25 mg/g.

20. A method of making hydrous metal oxide particles according to claim 1 comprising:
combining at least one oxygen-containing additive with at least one water soluble metal salt in an aqueous solvent to form a first solution wherein the oxygen-containing additive forms a complex with metal ions in the first solution; and
combining the first solution with at least one precipitant to obtain hydrous metal oxide particles by sol gel precipitation.

21. The method of claim 20, wherein the metal ion of the hydrous metal oxide particles comprises a zirconium ion, a hafnium ion, a titanium ion, a tin ion, or a lead ion.

22. The method of claim 20, wherein the metal ion is a zirconium ion and the water soluble metal salt is a zirconium salt.

23. The method of claim 20, wherein the water soluble metal salt is zirconium oxychloride.

24. The method of claim 20, wherein the precipitant has a molarity of from about 5 moles/L to about 25 moles/L.

25. The method of claim 20, wherein the precipitant is an alkali solution.

26. The method of claim 25, wherein the alkali solution is sodium hydroxide.

27. The method of claim 20, wherein the water soluble metal salt is zirconium oxychloride and the zirconium oxychloride and precipitant are introduced at a molar ratio of metal salt to precipitant of from about 0.1:1 to about 0.5:1.

28. The method of claim 20, wherein the water soluble metal salt is zirconium oxychloride and the zirconium oxychloride is present in the aqueous solvent at a concentration of from about 0.5 to about 2.0 g/ml.

29. The method of claim 20, wherein the aqueous solvent is deionized water or reverse osmosis water.

30. The method of claim 20, wherein the water soluble metal salt is dissolved in the aqueous solvent and then the oxygen-containing additive is added to form the first solution.

31. The method of claim 20, wherein the water soluble metal salt is present in the aqueous solvent at a saturation concentration.

32. The method of claim 20, wherein the oxygen-containing additive is dissolved in the aqueous solvent and then the water soluble metal salt is added to form the first solution.

33. The method of claim 20, wherein the oxygen-containing additive is present in the first solution in a molar amount sufficient to prevent gelation of the particles.

34. The method of claim 20, wherein the oxygen-containing additive forms a soluble complex with the metal ion of the hydrous metal oxide.

35. The method of claim 20, wherein the oxygen-containing additive forms a temporary complex with the metal ion of the hydrous metal oxide in the solution such that the additive is removable from the particles with a washing step after precipitation.

36. The method of claim 20, wherein the oxygen-containing additive forms a permanent complex with the metal ion of the hydrous metal oxide.

37. The method of claim 20, wherein the first solution and the precipitant are combined by providing the precipitant in an aqueous solution and adding at least part of the first and at least part of the precipitant solution simultaneously to a reaction vessel so that the concentration of precipitant is kept constant in the reaction vessel during a period of time that the precipitant is added to the reaction vessel.

38. The method of claim 20, wherein said first solution is simultaneously added with a diluted solution of precipitant to the reaction vessel.

39. The method of claim 38, wherein the reaction vessel includes an agitator.

40. The method of claim 20, wherein a slurry containing at least a hydrous metal oxide gel precipitate is formed, and wherein the slurry is agitated.

41. The method of claim 40, further comprising filtering the slurry after mixing.

42. The method of claim 40, further comprising washing the slurry with deionized water (alkaline wash).

43. The method of claim 42, further comprising forming a filter cake.

44. The method of claim 43, further comprising transferring the filter cake back to deionized water to form a second slurry.

45. The method of claim 44, further comprising titrating the second slurry to lower pH to a value in a range of from about pH 2 to about pH 8 by addition of acid to remove precipitant cations (acid wash).

46. The method of claim 45, further comprising filtering the titrated or acid-washed slurry and drying the product until the moisture of the product is from about 10% to about 40% LOD in the form of free-flowing powder.

47. The method of claim 20, further comprising isolating and drying the resulting hydrous metal oxide particles to obtain a free flowing powder.

48. The method of claim 20, wherein the first solution is in the form of droplets before it is combined with the precipitant.

49. The method of claim 20, wherein the first solution obtained and the precipitant solution are combined so that metal ions and precipitant are present in a molar ratio of from about 0.1 to about 1 of metal to precipitant.

* * * * *